(12) United States Patent
McGonigle

(10) Patent No.: US 7,323,621 B2
(45) Date of Patent: Jan. 29, 2008

(54) METHOD OF DECREASING LIQUIRITIGENIN-DERIVED ISOFLAVONES RELATIVE TO TOTAL ISOFLAVONES IN PLANTS AND PLANTS PRODUCING REDUCED RATIO OF LIQUIRITIGENIN-DERIVED ISOFLAVONES RELATIVE TO TOTAL ISOFLAVONES

(75) Inventor: Brian McGonigle, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 569 days.

(21) Appl. No.: 10/734,947

(22) Filed: Dec. 11, 2003

(65) Prior Publication Data

US 2004/0128714 A1 Jul. 1, 2004

Related U.S. Application Data

(60) Provisional application No. 60/433,433, filed on Dec. 13, 2002.

(51) Int. Cl.
*A01H 5/00* (2006.01)
*A01H 5/10* (2006.01)
*C12N 15/63* (2006.01)
*C12N 15/82* (2006.01)

(52) U.S. Cl. ............... 800/285; 800/286; 800/287; 800/298; 800/312

(58) Field of Classification Search ............ 800/282, 800/285, 286, 298, 312
See application file for complete search history.

(56) References Cited

FOREIGN PATENT DOCUMENTS

WO WO 97/27295 A1 7/1997
WO WO 02/00904 A2 1/2002

OTHER PUBLICATIONS

Wang et al. AOCS Press, 2000 vol. 77 No. 5, pp. 483-487.*
Plant Cell Reports EPUB Jan. 5, 2007, pp. 1-9.*
Chigen Tsukamoto et al., Factors affecting isoflavone content in soybean seeds: changes in isoflavones, saponins, and composition of fatty acids at different temperatures during seed development, J. Agric. Food Chem., 43:1184-1192, 1995.
Roland Welle et al., Induced plant responses to pathogen attack, Eur. J. Biochem., 196:423-430, 1991.
Chunyang Wang et al., Isoflavone Content Among Maturity Group 0 to 11 Soybeans, JAOCS, 77(5):483-487, 2000.
Huei-Ju Wang et al., Isoflavone Composition of American and Japanese Soybeans in Iowa: Effects of Variety, Crop Year, and Location, J. Agric. Food Chem., 42:1674-1677, 1994.
Kazuyoshi Okubo et al., Components Responsible for the Undesirable Taste of Soybean Seeds, Biosci. Biotech. Biochem., 56(1):99-103, 1992.
National Center for Biotechnology Information General Identifier No. 537298, Accession No. AAB41556, Jan. 30, 1997, G. M. Ballance et al., Medicago sativa cDNAs encoding chalcone reductase.
National Center for Biotechnology Information General Identifier No. 20147510, Accession No. AAM12529, Mar. 18, 2003, J. H. Jeon et al., Molecular cloning of chalcone reductase gene from Pueraria Iobata.
National Center for Biotechnology Information General Identifier No. 99953, Accession No. S14222, Sep. 10, 1999, R. Welle et al., Induced plant responses to pathogen attack.
Richard A. Dixon et al., Molecular of Interest—Genistein, Phytochemistry, 60:205-211, 2002.
Akinwunmi Olumide Latunde-Dada et al., Flavonoid 6-Hydroxylase from Soybean (Glycine max L.), a Novel Plant P-450 Monooxygenase, J. Biol. Chem., 276(3):1688-1695, 2001.
Roland Welle et al., Isolation of a novel NADPH-dependent reductase which coacts with chalcone synthase in the biosynthesis of 6'-deoxychalcone, FEBS Letters, 236(1):221-225, 1988.
Richard A. Dixon et al., Stress-Induced Phenylpropanoid Metabolism, The Plant Cell, 7-1085-1097, 1995.
Patricia A. Murphy et al., Isoflavones in Retail and Institutional Soy Foods, J. Agric. Food Chem., 47:2697-2704, 1999.
Oliver Yu et al., Metabolic engineering to increase isoflavone biosynthesis in soybean seed, Phytochemistry 63, pp. 753-763, 2003.

* cited by examiner

*Primary Examiner*—Russell P. Kallis

(57) ABSTRACT

This invention pertains to methods for decreasing the ratio of liquiritigenin-derived isoflavones relative to total isoflavone levels in isoflavonoid-producing plants and plant parts by transforming plants with a recombinant DNA construct comprising a nucleic acid sequence of at least 200 nucleotides and having at least 75% sequence identity to a polynucleotide encoding a chalcone reductase. More preferably, this invention pertains to methods for decreasing the ratios of daidzein and glycitein and their conjugates relative to total isoflavone levels in soybean plants and soybean plant parts by transforming plants with a recombinant DNA construct comprising a nucleic acid sequence of at least 200 nucleotides and having at least 75% sequence identity to a polynucleotide encoding a chalcone reductase.

22 Claims, 4 Drawing Sheets

SEQUENCE LISTING

<160> NUMBER OF SEQ ID NOS: 8

<210> SEQ ID NO 1
<211> LENGTH: 7701
<212> TYPE: DNA
<213> ORGANISM: Artificial Sequence

```
<220> FEATURE:
<223> OTHER INFORMATION: Expression Vector pKS151
<220> FEATURE:
<221> NAME/KEY: misc_feature
<222> LOCATION: (6516)..(6516)
<223> OTHER INFORMATION: n = A, C, G, or T

<400> SEQUENCE: 1
cgcgcccgat catccggata tagttcctcc tttcagcaaa aaaccctca agacccgttt      60 agaggcccca aggggttatg ctagttattg ctcagcggtg gcagcagcca actcagcttc     120
ctttcgggct tgttagcag ccggatcgat ccaagctgta cctcactatt cctttgccct     180
cggacgagtg ctggggcgtc ggtttccact atcggcgagt acttctacac agccatcggt     240
ccagacggcc gcgcttctgc gggcgatttg tgtacgcccg acagtcccgg ctccggatcg    300
gacgattgcg tcgcatcgac cctgcgccca agctgcatca tcgaaattgc cgtcaaccaa    360
gctctgatag agttggtcaa gaccaatgcg gagcatatac gcccggagcc gcggcgatcc    420
tgcaagctcc ggatgcctcc gctcgaagta gcgcgtctgc tgctccatac aagccaacca    480
cggcctccag aagaagatgt tggcgacctc gtattgggaa tccccgaaca tcgcctcgct    540
ccagtcaatg accgctgtta tgcggccatt gtccgtcagg acattgttgg agccgaaatc    600
cgcgtgcacg aggtgccgga cttcggggca gtcctcggcc caaagcatca gctcatcgag    660
agcctgcgcg acggacgcac tgacggtgtc gtccatcaca gtttgccagt gatacacatg    720
gggatcagca atcgcgcata tgaaatcacg ccatgtagtg tattgaccga ttccttgcgg    780
tccgaatggg ccgaacccgc tcgtctggct aagatcggcc gcagcgatcg catccatagc    840
ctccgcgacc ggctgcagaa cagcgggcag ttcggtttca ggcaggtctt gcaacgtgac    900
accctgtgca cggcgggaga tgcaataggt caggctctcg ctgaattccc caatgtcaag    960
cacttccgga atcgggagcg cggccgatgc aaagtgccga taaacataac gatctttgta   1020
gaaaccatcg gcgcagctat ttacccgcag gacatatcca cgccctccta catcgaagct   1080
gaaagcacga gattcttcgc cctccgagag ctgcatcagg tcggagacgc tgtcgaactt   1140
ttcgatcaga aacttctcga cagacgtcgc ggtgagttca ggcttttcca tgggtatatc   1200
tccttcttaa agttaaacaa aattatttct agagggaaac cgttgtggtc tccctatagt   1260
gagtcgtatt aatttcgcgg gatcgagatc gatccaattc caatcccaca aaaatctgag   1320
cttaacagca cagttgctcc tctcagagca gaatcgggta ttcaacaccc tcatatcaac   1380
tactacgttg tgtataacgg tccacatgcc ggtatatacg atgactgggg ttgtacaaag   1440
gcggcaacaa acggcgttcc cggagttgca cacaagaaat ttgccactat tacagaggca   1500
agagcagcag ctgacgcgta cacaacaagt cagcaaacag acaggttgaa cttcatcccc   1560
aaaggagaag ctcaactcaa gcccaagagc tttgctaagg ccctaacaag cccaccaaag   1620
caaaaagccc actggctcac gctaggaacc aaaaggccca gcagtgatcc agccccaaaa   1680
gagatctcct ttgccccgga gattacaatg gacgatttcc tctatcttta cgatctagga   1740
aggaagttcg aaggtgaagg tgacgacact atgttcacca ctgataatga aaggttagc    1800 ctcttcaatt tcagaaagaa tgctgaccca cagatggtta gagaggccta cgcagcaggt   1860
ctcatcaaga cgatctaccc gagtaacaat ctccaggaga tcaaatacct tcccaagaag   1920
gttaaagatg cagtcaaaag attcaggact aattgcatca agaacacaga gaaagacata   1980
tttctcaaga tcagaagtac tattccagta tggacgattc aaggcttgct tcataaacca   2040
aggcaagtaa tagagattgg agtctctaaa aaggtagttc ctactgaatc taaggccatg   2100
```

```
catggagtct aagattcaaa tcgaggatct aacagaactc gccgtgaaga ctggcgaaca   2160
gttcatacag agtcttttac gactcaatga caagaagaaa atcttcgtca acatggtgga   2220
gcacgacact ctggtctact ccaaaaatgt caaagataca gtctcagaag accaaagggc   2280
tattgagact tttcaacaaa ggataatttc gggaaacctc ctcggattcc attgcccagc   2340
tatctgtcac ttcatcgaaa ggacagtaga aaaggaaggt ggctcctaca aatgccatca   2400
ttgcgataaa ggaaaggcta tcattcaaga tgcctctgcc gacagtggtc ccaaagatgg   2460
acccccaccc acgaggagca tcgtggaaaa agaagacgtt ccaaccacgt cttcaaagca   2520
agtggattga tgtgacatct ccactgacgt aagggatgac gcacaatccc actatccttc   2580
gcaagaccct tcctctatat aaggaagttc atttcatttg gagaggacac gctcgagctc   2640
atttctctat tacttcagcc ataacaaaag aactcttttc tcttcttatt aaaccatgaa   2700
aaagcctgaa ctcaccgcga cgtctgtcga agtttctg atcgaaaagt cgacagcgt     2760 ctccgacctg atgcagctct cggagggcga agaatctcgt gctttcagct tcgatgtagg   2820
agggcgtgga tatgtcctgc gggtaaatag ctgcgccgat ggtttctaca agatcgtta   2880 tgtttatcgg cactttgcat cggccgcgct cccgattccg gaagtgcttg acattgggga   2940
attcagcgag agcctgacct attgcatctc ccgccgtgca cagggtgtca cgttgcaaga   3000
cctgcctgaa accgaactgc ccgctgttct gcagccggtc gcggaggcca tggatgcgat   3060
cgctgcggcc gatcttagcc agacgagcgg gttcggccca ttcggaccgc aaggaatcgg   3120
tcaatacact acatggcgtg atttcatatg cgcgattgct gatccccatg tgtatcactg   3180
gcaaactgtg atggacgaca ccgtcagtgc gtccgtcgcg caggctctcg atgagctgat   3240
gctttgggcc gaggactgcc ccgaagtccg gcacctcgtg cacgcggatt tcggctccaa   3300
caatgtcctg acggacaatg gccgcataac agcggtcatt gactggagcg aggcgatgtt   3360
cggggattcc caatacgagg tcgccaacat cttcttctgg aggccgtggt tggcttgtat   3420
ggagcagcag acgcgctact cgagcggag gcatccggag cttgcaggat cgccgcggct   3480
ccgggcgtat atgctccgca ttggtcttga ccaactctat cagagcttgg ttgacggcaa   3540
tttcgatgat gcagcttggg cgcagggtcg atgcgacgca atcgtccgat ccggagccgg   3600
gactgtcggg cgtacacaaa tcgcccgcag aagcgcggcc gtctggaccg atggctgtgt   3660
agaagtactc gccgatagtg gaaaccgacg ccccagcact cgtccgaggg caaaggaata   3720
gtgaggtacc taaagaagga gtgcgtcgaa gcagatcgtt caaacatttg gcaataaagt   3780
ttcttaagat tgaatcctgt tgccggtctt gcgatgatta tcatataatt tctgttgaat   3840
tacgttaagc atgtaataat taacatgtaa tgcatgacgt tatttatgag atgggttttt   3900
atgattagag tcccgcaatt atacatttaa tacgcgatag aaaacaaaat atagcgcgca   3960
aactaggata aattatcgcg cgcggtgtca tctatgttac tagatcgatg tcgaatctga   4020
tcaacctgca ttaatgaatc ggccaacgcg cggggagagg cggtttgcgt attgggcgct   4080
cttccgcttc ctcgctcact gactcgctgc gctcggtcgt tcggctgcgg cgagcggtat   4140
cagctcactc aaaggcggta atacggttat ccacagaatc aggggataac gcaggaaaga   4200
acatgtgagc aaaaggccag caaaaggcca ggaaccgtaa aaaggccgcg ttgctggcgt   4260
ttttccatag gctccgcccc cctgacgagc atcacaaaaa tcgacgctca agtcagaggt   4320
ggcgaaaccc gacaggacta taaagatacc aggcgtttcc ccctggaagc tccctcgtgc   4380
gctctcctgt tccgaccctg ccgcttaccg gatacctgtc gcctttctc ccttcgggaa    4440 gcgtggcgct ttctcaatgc tcacgctgta ggtatctcag ttcggtgtag gtcgttcgct   4500
```

```
ccaagctggg ctgtgtgcac gaaccccccg ttcagcccga ccgctgcgcc ttatccggta   4560
actatcgtct tgagtccaac ccggtaagac acgacttatc gccactggca gcagccactg   4620
gtaacaggat tagcagagcg aggtatgtag gcggtgctac agagttcttg aagtggtggc   4680
ctaactacgg ctacactaga aggacagtat ttggtatctg cgctctgctg aagccagtta   4740
ccttcggaaa aagagttggt agctcttgat ccggcaaaca aaccaccgct ggtagcggtg   4800
gtttttttgt ttgcaagcag cagattacgc gcagaaaaaa aggatctcaa gaagatcctt   4860
tgatcttttc tacggggtct gacgctcagt ggaacgaaaa ctcacgttaa gggattttgg   4920
tcatgacatt aacctataaa aataggcgta tcacgaggcc ctttcgtctc gcgcgtttcg   4980
gtgatgacgg tgaaaacctc tgacacatgc agctcccgga cggtcaca gcttgtctgt   5040 aagcggatgc cgggagcaga caagcccgtc agggcgcgtc agcgggtgtt ggcgggtgtc   5100
ggggctggct taactatgcg gcatcagagc agattgtact gagagtgcac catatggaca   5160
tattgtcgtt agaacgcggc tacaattaat acataacctt atgtatcata cacatacgat   5220
ttaggtgaca ctatagaacg cgcgccgtc gacggatata atgagccgta aacaaagatg   5280
attaagtagt aattaatacg tactagtaaa agtggcaaaa gataacgaga aagaaccaat   5340
ttctttgcat tcggccttag cggaaggcat atataagctt tgattatttt atttagtgta   5400
atgatttcgt acaaccaaag catttattta gtactctcac acttgtgtcg cggccggagc   5460
tggtcatctc gctcatcgtc gagtcggcgg ccggagctgg tcatctcgct catcgtcgag   5520
tcggcggccg ccgactcgac gatgagcgag atgaccagct ccggccgccg actcgacgat   5580
gagcgagatg accagctccg gccgcttggg gggctatgga agactttctt agttagttgt   5640
gtgaataagc aatgttggga gaatcgggac tacttatagg ataggaataa aacagaaaag   5700
tattaagtgc taatgaaata tttagactga taattaaaat cttcacgtat gtccacttga   5760
tataaaaacg tcaggaataa aggaagtaca gtagaattta aaggtactct ttttatatat   5820
acccgtgttc tcttttttggc tagctagttg cataaaaaat aatctatatt tttatcatta   5880
ttttaaatat cttatgagat ggtaaatatt tatcataatt ttttttacta ttatttatta   5940
tttgtgtgtg taatacatat agaagttaat tacaaatttt atttactttt tcattatttt   6000
gatatgattc accattaatt tagtgttatt atttataata gttcattta atcttttttgt   6060 atatattatg cgtgcagtac ttttttccta catataacta ctattacatt ttatttatat   6120 aatatttta ttaatgaatt ttcgtgataa tatgtaatat tgttcattat tatttcagat   6180
tttttaaaaa tatttgtgtt attatttatg aaatatgtaa ttttttttagt atttgatttt   6240 atgatgataa agtgttctaa attcaaaaga aggggggaaag cgtaaacatt aaaaaacgtc   6300
atcaaacaaa aacaaaatct tgttaataaa gataaaactg tttgttttga tcactgttat   6360
ttcgtaatat aaaaacatta tttatattta tattgttgac aaccaaattt gcctatcaaa   6420
tctaaccaat ataatgcatg cgtggcaggt aatgtactac catgaactta agtcatgaca   6480
taataaaccg tgaatctgac caatgcatgt acctanctaa attgtatttg tgacacgaag   6540
caaatgattc aattcacaat ggagatggga aacaaataat gaagaaccca gaactaagaa   6600
agcttttctg aaaaataaaa taaaggcaat gtcaaaagta tactgcatca tcagtccaga   6660
aagcacatga tatttttta tcagtatcaa tgcagctagt tttattttac aatatcgata   6720
tagctagttt aaatatattg cagctagatt tataaatatt tgtgttatta tttatcatt   6780 gtgtaatcct gttttttagta ttttagtttta tatatgatga taatgtattc caaatttaaa   6840
```

-continued

```
agaagggaaa taaatttaaa caagaaaaaa agtcatcaaa caaaaaacaa atgaaagggt    6900
ggaaagatgt taccatgtaa tgtgaatgtt acagtatttc ttttattata gagttaacaa    6960
attaactaat atgattttgt taataatgat aaaatatttt ttttattatt atttcataat    7020
ataaaaatag tttacttaat ataaaaaaaa ttctatcgtt cacaacaaag ttggccacct    7080
aatttaacca tgcatgtacc catggaccat attaggtaac catcaaacct gatgaagaga    7140
taaagagatg aagacttaag tcataacaca aaaccataaa aaacaaaaat acaatcaacc    7200
gtcaatctga ccaatgcatg aaaaagctgc aatagtgagt ggcgacacaa agcacatgat    7260
tttcttacaa cggagataaa accaaaaaaa tatttcatga acaacctaga acaaataaag    7320
cttttatata ataaatatat aaataaataa aggctatgga ataatatact tcaatatatt    7380
tggattaaat aaattgttgg cggggttgat atatttatac acacctaaag tcacttcaat    7440
ctcattttca cttaactttt attttttttt tcttttttatt tatcataaag agaatattga   7500
taatatactt tttaacatat ttttatgaca tttttttattg gtgaaaactt attaaaaatc   7560
ataaattttg taagttagat ttatttaaag agttcctctt cttatttttaa attttttaat   7620 aaattttaa ataactaaaa tttgtgttaa aaatgttaaa aaatgtgtta ttaaccccttc    7680 tcttcgagga tccaagcttg g                                             7701

<210> SEQ ID NO 2
<211> LENGTH: 29
<212> TYPE: DNA
<213> ORGANISM: Artificial Sequence
<220> FEATURE:
<223> OTHER INFORMATION: Amplification primer chalcone reductase Not1
                        sense

<400> SEQUENCE: 2
gcggccgcat ggctgctgct attgaaatc                                       29

<210> SEQ ID NO 3
<211> LENGTH: 29
<212> TYPE: DNA
<213> ORGANISM: Artificial Sequence
<220> FEATURE:
<223> OTHER INFORMATION: Amplification primer chalcone reductase Not1
                        antisense

<400> SEQUENCE: 3
gcggccgccc tgctcgcacc tttcctcag                                       29

<210> SEQ ID NO 4
<211> LENGTH: 1410
<212> TYPE: DNA
<213> ORGANISM: Glycine max

<400> SEQUENCE: 4
acaagaagga tggtccaaaa gtatctaata ggccatctcg atctcatctg accaagcttc     60
ctggttagtt cctttgaatt gaataatata aaaaaaagaa gatgatggat gtgggtagag    120
ctcagtataa cccacctacc tccaattgct gacttttcaa aggccaaaca tgaagaaatg    180
ttgcagtata aaaaggggtg cccttcagtt atgtccatca acaaatattg gaatactaca    240
ctatacttgt caacccttg agagttagaa tggctgctgc tattgaaatc cccacaatag    300
tgtttccaaa ctcctctgcc aacagagga tgccagtggt tggaatggga tctgcccctg    360
acttcacatg caagaaagac acaaaggagg ctatcattga ggccgtgaaa cagggttaca    420
gacacttcga cactgctgct gcttatggct ctgaacaggc tctcggtgaa gctctcaagg    480
```

```
aagctatcca tcttggcctc gtctcccgcc aagacctctt tgtcacttcc aagctttggg      540
tcaccgaaaa tcatcctcat cttgtccttc ctgctttgcg caaatcactt aaaactcttc      600
aactagagta cttggacctg tatctcatcc actggcccct gagttctcag ccagggaagt      660
tctcatttcc aattgaagta gaagatctct tgccttttga cgtgaagggt gtgtgggaat      720
ccatggaaga gtgccagaaa cttggcctca ccaaagccat tggagtcagc aacttctctg      780
tcaagaagct tcagaatctg ctctctgttg ctaccatccg tcccgtggtc gatcaagtgg      840
agatgaacct tgcatggcaa cagaagaagc taagagagtt ctgcaaagaa atgggataa       900 tagtgactgc gttctctcca ctgaggaaag gtgcgagcag gggcccaaat gaagtgatgg      960
agaatgatgt gctgaaggag attgcagagg ctcatgggaa atccatagcc aggtgagtc     1020 tgagatggtt gtacgaacaa ggtgtgacat tgtgccaaa gagctacgat aaggagagga    1080
tgaaccagaa tctgcacatc tttgactggg cattgactga acaagatcat cacaaaataa    1140
gtcaaatcag ccagagccgt tgatcagcg gacccaccaa accacaactc gctgatctct    1200
gggatgatca aatataaact atttactact atgcagctcc cactctatt tttataatcca    1260 tcttttacc tcttgtttca ttttacgttt aaataattca tgccatgcca cttcttattt     1320
tagatttcac aatcaataaa ctaggcacgc gcggcacatg atatgaataa actatgttca    1380
attttttttt caaaaaaaaa aaaaaaaaa                                      1410

<210> SEQ ID NO 5
<211> LENGTH: 22
<212> TYPE: DNA
<213> ORGANISM: Artificial Sequence
<220> FEATURE:
<223> OTHER INFORMATION: Amplification primer Primer3

<400> SEQUENCE: 5
cacgggacgg atggtagcaa ca                                               22

<210> SEQ ID NO 6
<211> LENGTH: 25
<212> TYPE: DNA
<213> ORGANISM: Artificial Sequence
<220> FEATURE:
<223> OTHER INFORMATION: Amplification primer Primer4

<400> SEQUENCE: 6
ccgattctcc caacattgct tattc                                            25

<210> SEQ ID NO 7
<211> LENGTH: 154
<212> TYPE: DNA
<213> ORGANISM: Artificial Sequence
<220> FEATURE:
<223> OTHER INFORMATION: Artificial sequence containing a NotI site
                        flanked by two 36-nucleotide repeats and having
                        an EagI site at each end.

<400> SEQUENCE: 7
cggccggagc tggtcatctc gctcatcgtc gagtcggcgg ccggagctgg tcatctcgct      60
catcgtcgag tcggcggccg ccgactcgac gatgagcgag atgaccagct ccggccgccg     120
actcgacgat gagcgagatg accagctccg gccg                                 154

<210> SEQ ID NO 8
<211> LENGTH: 10
<212> TYPE: PRT
```

```
<213> ORGANISM: Artificial Sequence
<220> FEATURE:
<223> OTHER INFORMATION: Translation of one 30 nucleotide repeat found
                        in pKS151

<400> SEQUENCE: 8

Glu Leu Val Ile Ser Leu Ile Val Glu Ser
1               5                   10
```

METHOD OF DECREASING LIQUIRITIGENIN-DERIVED ISOFLAVONES RELATIVE TO TOTAL ISOFLAVONES IN PLANTS AND PLANTS PRODUCING REDUCED RATIO OF LIQUIRITIGENIN-DERIVED ISOFLAVONES RELATIVE TO TOTAL ISOFLAVONES

This application claims the benefit of U.S. Provisional Application No. 60/433,433, filed 13 Dec. 2002. The entire content of this application is hereby incorporated by reference.

This invention relates to altering isoflavone levels in an isoflavonoid-producing plant and, in particular, to a method for decreasing the ratio of liquiritigenin-derived isoflavones relative to total isoflavone levels in isoflavonoid-producing plants and plant parts by transforming plants with a recombinant DNA construct comprising a nucleic acid sequence of at least 200 nucleotides and having at least 75% sequence identity to a polynucleotide encoding a chalcone reductase.

Isoflavonoids represent a class of secondary metabolites produced predominantly in legumes by a branch of the phenylpropanoid pathway and include such compounds as isoflavones, isoflavanones, rotenoids, pterocarpans, isoflavans, quinone derivatives, 3-aryl-4-hydroxycoumarins, 3-arylcoumarins, isoflav-3-enes, coumestans, alpha-methyldeoxybenzoins, 2-arylbenzofurans, isoflavanol, coumaronochromone and the like. In plants, these compounds are known to be involved in interactions with other organisms and to participate in the defense responses of legumes against phytopathogenic microorganisms (Dewick, P. M. (1993) in The Flavonoids, Advances in Research Since 1986, Harborne, J. B. Ed., pp. 117-238, Chapman and Hall, London). Isoflavonoid-derived compounds also are involved in symbiotic relationships between roots and rhizobial bacteria that eventually result in nodulation and nitrogen-fixation (Phillips, D. A. (1992) in *Recent Advances in Phytochemistry*. Vol. 26, pp 201-231, Stafford, H. A. and Ibrahim, R. K., Eds, Plenum Press, New York), and overall they have been shown to act as antibiotics, repellents, attractants, and signal compounds (Barz, W. and Welle, R. (1992) *Phenolic Metabolism in Plants*, pp 139-164, Ed by H. A. Stafford and R. K. Ibrahim, Plenum Press, New York).

Isoflavonoids have also been reported to have physiological activity in animal and human studies. For example, it has been reported that the isoflavones found in soybean seeds possess antihemolytic (Naim, M., et al. (1976) *J. Agric. Food Chem.* 24:1174-1177), antifungal (Naim, M., et al. (1974) *J. Agr. Food Chem.* 22:806-810), estrogenic (Price, K. R. and Fenwick, G. R. (1985) *Food Addit. Contam.* 2:73-106), tumor-suppressing (Messina, M. and Barnes, S. (1991) *J. Natl. Cancer Inst.* 83:541-546; Peterson, G., et al. (1991) *Biochem. Biophys. Res. Commun.* 179:661-667), hypolipidemic (Mathur, K., et. al. (1964) *J. Nutr.* 84:201-204), and serum cholesterol-lowering (Sharma, R. D. (1979) *Lipids* 14:535-540) effects. In addition, both epidemiological and dietary-intervention studies indicate that when isoflavones in soybean seeds and in subsequent protein products prepared from the seeds are part of the human dietary intake, those products provide many significant health benefits (Messina, M. J. (1999) *Am. J. Clin. Nutr.* 70:439S-450S; Walker, C. L. (2002) *Recent Prog. Horm. Res.*57:277-294; Davis, S. R. et al. (1999) *Recent Prog. Horm. Res.* 54, 185-210; Messina, M. J. (1999) *Am. J. Clin. Nutr.* 70 (suppl): 439S-450S; Watanabe, S. et al. (2002) *Biomed. Pharmacother.* 56, 302-312; Clarkson, T. B. (2002) *J. Nutr.* 132:566S-569S).

Soybean seeds contain three types of isoflavone aglycones: daidzein, genistein, and glycitein. However, free isoflavones rarely accumulate to high levels in soybeans; instead they are usually conjugated to carbohydrates or organic acids. Each aglycone can be found in three different forms: glucoside conjugates known as daidzin, genistin, and glycitin; malonylglucoside conjugates known as 6"-O-malonyldaidzin, 6"-O-malonylgenistin and 6"-O-malonylglycitin. During processing acetylglucoside conjugates known as 6'-O-acetyidaidzin, 6'-O-acetylgenistin, and 6'-O-acetylglycitin are sometimes produced.

The total isoflavone levels as well as the distribution among different aglycones is quite variable in soybean seeds and is affected by both genetics and environmental conditions such as growing location and temperature during seed fill (Tsukamoto, C., et al. (1995) *J. Agric. Food Chem.* 43:1184-1192; Wang, H. and Murphy, P. A. (1994) *J. Agric. Food Chem.* 42:1674-1677). In addition, isoflavonoid content in legumes can be stress-induced by pathogen attack, wounding, high UV light exposure and pollution (Dixon, R. A. and Paiva, N. L. (1995) *Plant Cell* 7:1085-1097). The genistein isoflavonoid forms make up the most abundant group in most food products, while the daidzein and the glycitein forms are present in lower levels (Murphy, P. A. (1999) *J. Agric. Food Chem.* 47:2697-2704).

The biosynthetic pathway for isoflavonoids in soybean and their relationship with several other classes of phenylpropanoids is presented in FIG. 1. Production of coumaryl-CoA from phenylalanine requires phenylalanine ammonia lyase to convert phenylalanine to cinnamate, cinnamic acid hydroxylase to convert cinnamate to p-coumarate, and coumarate:CoA ligase to convert p-coumarate to p-coumaroyl-CoA. Lignins may be produced from p-coumaroyl-CoA or from p-coumarate. Soybean chalcone synthase catalyzes the conversion of p-coumaroyl-CoA to 4, 2', 4', 6'-tetrahydroxychalcone that is isomerized in a reaction catalyzed by chalcone isomerase to naringenin, the precursor to genistein, flavones, flavonols, and others. Alternatively, chalcone reductase together with a chalcone synthase and NADPH as a cofactor, act in the formation of isoliquiritigenin which is then isomerized to form liquiritigenin, the precursor to daidzein, glycitein, and the pterocarpan phytoalexins (Welle, R. and Grisebach, H. (1988) *FEBS Lett.* 236:221-225). Chalcone reductase is also known as deoxychalcone synthase and is abbreviated CHR. Polynucleotide sequences encoding CHR have been reported for soybean (*Glycine max*; NCBI General Identifier No. 99953), kudzu vine (*Pueraria montana* var. *lobata*; NCBI General Identifier No. 20147510), and alfalfa (*Medicago sativa* subsp. *sativa*; NCBI General Identifier No. 537298), as well as others. Glycitein synthesis is not yet clearly defined, but is likely made from liquiritigenin (Latunde-Dada, A. O. et al. (2001) *J. Biol. Chem.* 276,1688-1685). Genistein synthesis shares the naringenin intermediate with the flavonol/anthocyanin branch of the phenylpropanoid pathway. In all cases the unique aryl migration reaction to create the isoflavones is mediated by isoflavone synthase, or IFS. Sequences encoding the IFS gene have been identified for licorice (Akashi, T. et al. (1999) *Plant Physiol.* 121:821-828) and soybean (Steele, C. L. (1999) *Arch Biochem. Biophys.* 367:146-150; Jung, W. et al. (2000) *Nature Biotech.* 18:208-212; editor's correction: *Nature Biotech.* 18:559).

The use of sequences with low homology to CHR to control strawberry ripening is suggested in PCT publication No. WO 97/27295 (published Jul. 31, 1997). In the publication 27 ripening-related clones were selected and compared with sequences in the EMBL database using the GCG software. One of these clones was identified as having homology to a polynucleotide sequence encoding CHR. No additional information is given about the strawberry CHR or its use in regulating fruit ripening. However strawberry does not make isoflavonoids and would therefore not be expected to make CHR.

The physiological benefits associated with isoflavonoids in both plants and humans make the manipulation of their contents in crop plants highly desirable. The human body responds differently to different isoflavones. Although both daidzein and genistein act as phytoestrogens, genistein seems to have other specific abilities such as DNA topoisomerase and tyrosine protein kinase as well as antioxidant and cell cycle inhibitor activity (Dixon, R. A. and Ferreira, D. (2002) *Phytochemistry* 60:205-211). At times it may be desirable to consume genistein and not daidzein.

The flavor of soybeans is affected by multiple factors. Among these are isoflavones, and in particular daidzin and genistin. Okubo et al. identified the compounds in soybean that produce a dry mouth feel and reported a quantitative measurement (Okubo et al. (1992) *Biosci. Biotech. Biochem.* 56:99-103). In this study the concentration at which the dry mouth feel was first detected was reported as the threshold value. The threshold value for detection of daidzin was found to be $10^{-5}$ to $10^{-6}$ M while the threshold value for daidzein, its aglycone, was $10^{-6}$ M. The threshold value for genistin was $10^{-5}$ M and the one for genistein was $10^{-4}$ M. Thus, reduction of the levels of daidzin and its aglycone without effecting the levels of genistin or its aglycone will result in soybeans with better flavor and still improved health benefits. Because CHR catalyzes the committed step in the production of liquiritigenin-derived isoflavones, suppression of this enzyme will result in soybeans with lower levels of liquiritigenin-derived isoflavones without affecting the naringenin-derived isoflavones.

SUMMARY OF THE INVENTION

The present invention includes a method for decreasing the ratio of liquiritigenin-derived isoflavones relative to total isoflavone levels in an isoflavonoid-producing plant the method comprising: a) transforming a plant cell with a recombinant construct comprising a promoter operably linked to a nucleic acid sequence of at least 200 nucleotides having at least 75% sequence identity to SEQ ID NO:4; b) regenerating a transformed plant from the transformed plant cell of (a); and c) evaluating the transformed plant obtained from step (b) for a reduced ratio of liquiritigenin-derived isoflavones relative to total isoflavone levels as compared to the ratio of liquiritigenin-derived isoflavones relative to total isoflavone levels in an untransformed plant.

In a second embodiment, this invention includes an isoflavonoid-producing plant made by the method of the invention wherein the plant has a reduced ratio of liquiritigenin-derived isoflavones relative to total isoflavone levels as compared to the ratio of liquiritigenin-derived isoflavones relative to total isoflavone levels in an untransformed plant. Isoflavonoid-producing plants of interest include soybean, clover, mung bean, lentil, hairy vetch, alfalfa, lupine, sugar beet, and snow pea. Seeds or plant parts of such plants are also of interest.

In a third embodiment, this invention includes isoflavonoid-containing products such as protein isolate, protein concentrate, meal, grits, full fat and defatted flours, textured proteins, textured flours, textured concentrates, textured isolates, soymilk, tofu, fermented soy products, and whole bean soy products which are obtained from seeds or plant parts of the invention.

In a fourth embodiment, this invention includes a food, nutritional supplement, food bar, or beverage which has incorporated therein an isoflavonoid-containing product of the invention.

In a fifth embodiment, this invention includes an isoflavonoid-producing plant comprising in its genome a recombinant construct comprising a promoter operably linked to a nucleic acid sequence of at least 200 nucleotides and having at least 75% sequence identity to SEQ ID NO:4 wherein the plant has a reduced ratio of liquiritigenin-derived isoflavones relative to total isoflavone levels as compared to the ratio of liquiritigenin-derived isoflavones relative to total isoflavone levels in an untransformed plant.

In a sixth embodiment, this invention includes a method of producing an isoflavonoid-containing product having a reduced ratio of liquiritigenin-derived isoflavones relative to total isoflavone levels which comprises: (a) cracking the seeds of the invention to remove the meats from the hulls; and (b) flaking the meats obtained in step (a) to obtain the desired flake thickness.

BRIEF DESCRIPTION OF THE DRAWINGS AND SEQUENCE LISTINGS

The invention can be more fully understood from the following detailed description and the accompanying Sequence Listing which form a part of this application.

Figure 1:
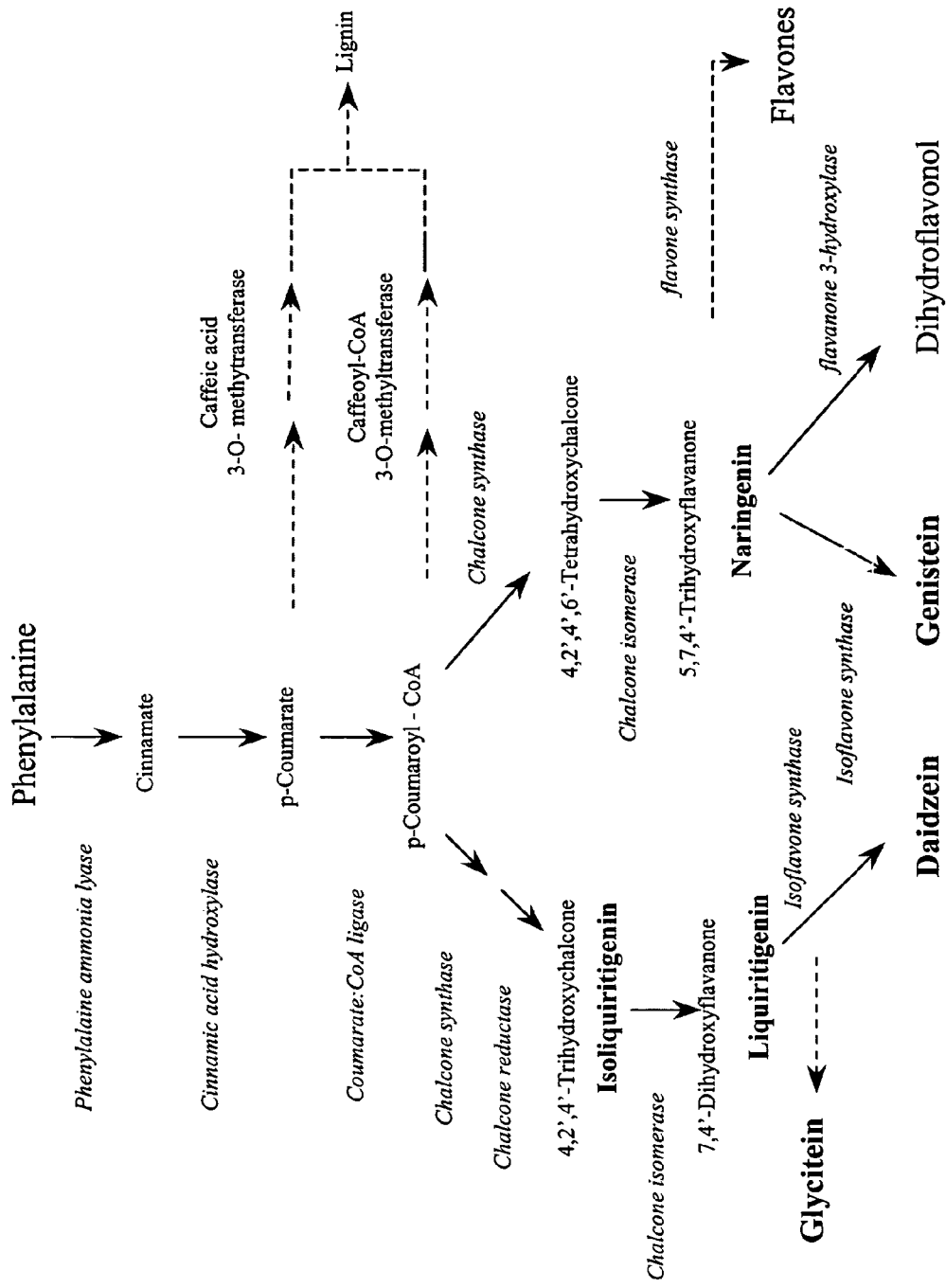
FIG. 1 depicts the soybean biosynthetic pathway from phenylalanine to glycitein, daidzein, genistein, and dihydroflavonol.

The following sequence descriptions and Sequences Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO:1 is the nucleotide sequence of plasmid pKS151 a seed-specific gene silencing vector.

SEQ ID NO:2 is the nucleotide sequence of primer chalcone reductase-Not1-sense, used to amplify a portion of the gene encoding chalcone reductase in clone src3c.pk009.e4.

SEQ ID NO:3 is the nucleotide sequence of primer chalcone reductase-Not1-antisense, used to amplify a portion of the gene encoding chalcone reductase in clone src3c.pk009.e4.

SEQ ID NO:4 is the nucleotide sequence of a contig comprising the cDNA insert in plasmid src3c.pk009.e4 as well as other soybean ESTs. Nucleotides 270 through 1214 are the coding region for a chalcone reductase.

SEQ ID NO:5 is the nucleotide sequence of primer 3, used to detect the presence of the chalcone reductase construct in transformed plants.

SEQ ID NO:6 is the nucleotide sequence of primer 4, used to detect the presence of the chalcone reductase construct in transformed plants.

SEQ ID NO:7 is the nucleotide sequence of nucleotides 5451-5567 from SEQ ID NO:1. This nucleotide sequence corresponds to the polynucleotide fragment consisting essentially of a unique Not 1 restriction endonuclease site surrounded by nucleotides that promote formation of a stem structure which are flanked by Eag I restriction endonuclease sites.

SEQ ID NO:8 is the amino acid sequence that would result from translating one 30-nucleotide sequence repeat in plasmid pKS151, for example, from nucleotides 5457-5486 of SEQ ID NO:1.

DETAILED DESCRIPTION OF THE INVENTION

All patents, patent applications, and publications cited are incorporated herein by reference in their entirety.

In the context of this disclosure, a number of terms shall be utilized.

The term "isoflavonoid(s)" refers to a large group of polyphenolic compounds, based on a common diphenylpropane skeleton, which occur naturally in plants. "Isoflavones" are the most abundant of the natural isoflavonoids with over 160 isoflavone aglycones now recognized. This term, as used herein, includes, but is not limited to, the three types of isoflavone aglycones found in soybean daidzein, genistein, and glycitein. Free isoflavones rarely accumulate to high levels in soybeans; instead they are usually conjugated to carbohydrates or organic acids. The term isoflavones includes all of the conjugates such as the glucoside conjugates daidzin, genistin, and glycitin; malonylglucoside conjugates known as 6"-O-malonyldaidzin, 6"-O-malonylgenistin, and 6"-O-malonylglycitin; and acetylglucoside conjugates known as 6'-O-acetyldaidzin, 6'-O-acetylgenistin, and 6'-O-acetylglycitin that are sometimes produced during processing.

"Liquiritigenin-derived isoflavones" as used herein refers to those isoflavones produced in a branch of the phenylpropanoid pathway involving a chalcone reductase-mediated reaction. Examples of liquiritigenin-derived isoflavones include, but are not limited to, daidzein, formononetin, isoformononetin, dimethyidaidzein, 7,2',4'-trihydroxyisoflavone, 2'-hydroxyformononetin, theralin, 3'hydroxydaidzein, 3'-hydroxyformononetin (calycosin), sayanedin, cabreuvin, pseudobaptigenin, 7-methoxy-3'4'-methylenedioxyisoflavone, koparin, 2-hydroxy-7,3',4'-trimethoxyisoflavone, glyzaglabrin, 7,2',4',5'-tetramethoxyisoflavone, gliricidin, texasin, glyitein, kakkatin, aformosin, odoratin, cladrastin, 6,7,3',4'-tetramethoxyisoflavone, fujikenetin, dalpatein, milidurone, retusin, 8-methylretusin and their conjugates (The Flavonoids: Advances in Research Chapman and Hall Ltd, 1982 edited by J. B. Harborne and T. J. Mabry—chapter Isoflavonoids P. M. Dewick pp 535-632).

"Total isoflavone levels" refers to all the isoflavones produced by an isoflavonoid-producing plant.

The term "isoflavonoid-producing plant" refers to a plant in which isoflavonoids naturally occur. Examples of isoflavonoid-producing plants include, but are not limited to, soybean, clover, mung bean, lentil, hairy vetch, alfalfa, lupine, sugar beet, and snow pea. In a more preferred embodiment, the preferred isoflavonoid-producing plant would be soybean. Examples of other isoflavonoid-producing plants can be found in WO 93/23069, published Nov. 25, 1993, the disclosure of which is hereby incorporated by reference.

The term "chalcone reductase" or "deoxychalcone synthase" refers to the polypeptide or enzyme that, together with a chalcone synthase and NADPH as a cofactor acts in the formation of isoliquiritigenin which is then isomerized to form liquiritigenin, the precursor to daidzein, glycitein, and the pterocarpan phytoalexins. Chalcone reductase is abbreviated CHR.

The terms "CHR construct", "chalcone reductase construct", and "plasmid AC23" are used interchangeably herein.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N"for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. (1989) *Biochemistry of Plants* 15:1-82.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989. Transformation methods are well known to those skilled in the art and are described below.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product e.g., a mRNA or a protein (precursor or mature).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J.* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999 and more recently, Applicants' assignee's own WO 02/00904 published on Jan. 3, 2002). This increases the frequency of co-suppression in the recovered transgenic plants. Hairpin structures may contain the target RNA forming either the stem or the loop of the hairpin. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although genetic evidence has begun to unravel this complex situation (Elmayan et al. (1998) *Plant Cell* 10:1747-1757).

The polynucleotide sequences used for suppression do not necessarily have to be 100% complementary to the polynucleotide sequences found in the gene to be suppressed. For example, suppression of all the subunits of the soybean seed storage protein β-conglycinin has been accomplished using a polynucleotide derived from a portion of the gene encoding the α subunit (U.S. Pat. No. 6,362,399). β-conglycinin is a heterogeneous glycoprotein composed of varying combinations of three highly negatively charged subunits identified as α, α' and β. The polynucleotide sequences encoding the α and α' subunits are 85% identical to each other while the polynucleotide sequences encoding the β subunit are 75 to 80% identical to the α and α' subunits. Thus, polynucleotides that are at least 75% identical to a region of the polynucleotide that is target for suppression have been shown to be effective in suppressing the desired target. The polynucleotide should be at least 80% identical, preferably at least 90% identical, most preferably at least 95% identical, or the polynucleotide may be 100% identical to the desired target.

The present invention includes a method for decreasing the ratio of liquiritigenin-derived isoflavones relative to total isoflavone levels in an isoflavonoid-producing plant the method comprising: a) transforming a plant cell with a recombinant construct comprising a promoter operably linked to a nucleic acid sequence of at least 200 nucleotides having at least 75% sequence identity to SEQ ID NO:4; b) regenerating a transformed plant from the transformed plant cell of (a); and c) evaluating the transformed plant obtained from step (b) for a reduced ratio of liquiritigenin-derived isoflavones relative to total isoflavone levels as compared to the ratio of liquiritigenin-derived isoflavones relative to total isoflavone levels in an untransformed plant.

Examples of isoflavonoid-producing plants which can be used to practice the invention include, but are not limited to, soybean, clover, mung bean, lentil, hairy vetch, alfalfa, lupine, sugar beet, and snow pea.

Any promoter can be used in accordance with the method of the invention. Thus, the origin of the promoter chosen to drive expression of the coding sequence is not important as long as it has sufficient transcriptional activity to accomplish the invention by expressing translatable mRNA for the desired nucleic acid fragments in the desired host tissue. Either heterologous or non-heterologous (i.e., endogenous) promoters can be used to practice the invention. The promoter for use in the present invention may be selected from the group consisting of a seed-specific promoter, root-specific promoter, vacuole-specific promoter, and an embryo-specific promoter.

Among the most commonly used promoters are the nopaline synthase (NOS) promoter (Ebert et al. (1987) *Proc. Natl. Acad. Sci. U.S.A.* 84:5745-5749), the octapine synthase (OCS) promoter, caulimovirus promoters such as the cauliflower mosaic virus (CaMV) 19S promoter (Lawton et al. (1987) *Plant Mol. Biol.* 9:315-324), the CaMV 35S promoter (Odell et al. (1985) *Nature* 313:810-812), and the figwort mosaic virus 35S promoter, the light inducible promoter from the small subunit of rubisco, the Adh promoter (Walker et al. (1987) *Proc. Natl. Acad. Sci. U.S.A.* 84:6624-66280, the sucrose synthase promoter (Yang et al. (1990) *Proc. Natl. Acad. Sci. U.S.A.* 87:4144-4148), the R gene complex promoter (Chandler et al. (1989) *Plant Cell* 1:1175-1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. (1982) *Cell* 29:1015-1026). A plethora of promoters is described in WO 00/18963, published on Apr. 6, 2000, the disclosure of which is hereby incorporated by reference.

Examples of a seed-specific promoter include, but are not limited to, the promoter for β-conglycinin (Chen et al. (1989) *Dev. Genet* 10: 112-122), the napin promoter, and the phaseolin promoter. Other tissue-specific promoters that may be used to accomplish the invention include, but are not limited to, the chloroplast glutamine synthase (GS2) promoter (Edwards et al. (1990) *Proc. Natl. Acad. Sci. U.S.A.* 87:3459-3463), the chloroplast fructose-1,6-biophosphatase promoter (Lloyd et al. (1991) *Mol. Gen. Genet.* 225:209-2216), the nuclear photosynthetic (ST-LS1) promoter (Stockhaus et al. (1989) *EMBO J.* 8:2445-2451), the serine/threonine kinase (PAL) promoter, the glucoamylase promoter, the promoters for the Cab genes (cab6, cab-1, and cab-1R, Yamamoto et al. (1994) *Plant Cell Physiol.* 35:773-778; Fejes et al. (1990) *Plant Mol. Biol.* 15:921-932; Lubberstedt et al. (1994) *Plant Physiol.* 104:997-1006; Luan et al. (1992) *Plant Cell* 4:971-981), the pyruvate orthophosphate dikanase promoter (Matsuoka et al. (1993) *Proc. Natl. Acad. Sci. U.S.A.* 90:9586-9590), the LhcB promoter (Cerdan et al. (1997) *Plant Mol. Biol.* 33:245-255), the PsbB promoter (Kretsch et al. (1995) *Plant Mol. Biol.* 28:219-229), the SUC2 sucrose H+ symporter promoter (Truernit et al. (1995) *Planta* 196:564-570), and the promoters for the thylakoid membrane genes (psaD, psaF, psaE, PC, FNR, atpC, atpD), etc.

The promoter is then operably linked, in a sense or antisense orientation, using conventional means well known to those skilled in the art to a nucleic acid sequence of at least 200 nucleotides having at least 75% sequence identity to SEQ ID NO:4.

Suppression in general is described above. However, in a preferred embodiment, the recombinant construct comprises a stem-loop structure as described in PCT publication WO 02/00904, published Jan. 3, 2002. WO 02/00904 discloses that suitable nucleic acid sequences and their reverse complement can be used to alter the expression of any homologous, endogenous RNA (i.e., the target RNA) which is flanked by the suitable nucleic acid sequence and its reverse complement. The suitable nucleic acid sequence and its reverse complement can be unrelated to any endogenous RNA in the host, can be transcribed for by any nucleic acid sequence in the genome of the host provided that nucleic acid sequence is not transcribed to any target mRNA or any sequence that is substantially similar to the target mRNA, or can be translated into a synthetic or non-naturally occurring polypeptide. What is presented in WO 02/00904 is a very efficient and robust approach to achieving single, or multiple, gene co-suppression using single plasmid transformation. Such constructs are composed of promoters linked to mRNA(s) coding regions, or fragments thereof, that are targeted for suppression, and short complementary sequences that are unrelated to the targets. The complementary sequences can be oriented both 5', both 3', or on either side of the target sequence. The complementary sequences are preferred to be about 40-50 nucleotides in length, or more preferably 50-100 nucleotides in length, or most preferably at least or greater than 100-300 nucleotides.

The complementary sequences are unrelated to the target, but can come from any other source. Preferred embodiments of these sequences include, but are not limited to, plant sequences, bacterial sequences, animal sequences, viral or phage sequences, or completely artificial, i.e. non-naturally occurring, sequences not known to occur in any organism. These complementary sequences can be synthesized using conventional means well known to those skilled in the art. Non-naturally complementary regions which can be used to practice the invention include, but are not limited to, a polynucleotide that may be translated into the polypeptide Glu Leu Val Ile Ser Leu Ile Val Glu Ser ("ELVISLIVES"; shown in SEQ ID NO:8).

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya (Ling, K. et al. (1991) Bio/technology 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28). Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. al. (1988) *Bio/Technology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, N.Y. (1997)).

In still another aspect, this invention includes an isoflavonoid-producing plant made by any of the instant methods wherein the plant has a reduced ratio of liquiritigenin-derived isoflavones relative to total isoflavone levels as compared to the ratio of liquiritigenin-derived isoflavones relative to total isoflavone levels in an untransformed plant.

In still a further aspect, there is included an isoflavonoid-producing plant comprising in its genome a recombinant construct comprising a promoter operably linked to a nucleic acid sequence of at least 200 nucleotides and having at least 75% sequence identity to SEQ ID NO:4 wherein the plant has a reduced ratio of liquiritigenin-derived isoflavones relative to total isoflavone levels as compared to the ratio of liquiritigenin-derived isoflavones relative to total isoflavone levels in an untransformed plant.

Also within the scope of this invention are seeds or plant parts obtained from such transformed plants. Plant parts include differentiated and undifferentiated tissues, including but not limited to, roots, stems, shoots, leaves, pollen, seeds, tumor tissue, and various forms of cells and culture such as single cells, protoplasts, embryos, and callus tissue. The plant tissue may be in plant or in organ, tissue or cell culture.

In a still further aspect, this invention includes an isoflavonoid-containing product having a reduced ratio of liquiritigenin-derived isoflavones relative to total isoflavone levels obtained from the seeds or plant parts of the invention.

Methods for obtaining such products are well known to those skilled in the art. For example, in the case of soybean, such products can be obtained in a variety of ways. Conditions typically used to prepare soy protein isolates have been described by [Cho, et al, (1981) U.S. Pat. No. 4,278,597; Goodnight, et al. (1978) U.S. Pat. No. 4,072,670]. Soy protein concentrates are produced by three basic processes: acid leaching (at about pH 4.5), extraction with alcohol (about 55-80%), and denaturing the protein with moist heat prior to extraction with water. Conditions typically used to prepare soy protein concentrates have been described by Pass [(1975) U.S. Pat. No. 3,897,574] and Campbell et al. [(1985) in New Protein Foods, ed. by Altschul and Wilcke, Academic Press, Vol. 5, Chapter 10, *Seed Storage Proteins*, pp 302-338].

"Isoflavonoid-containing protein products" can be defined as those items produced from seed or other plant part of a suitable plant which are used in feeds, foods and/or beverages. One of the plants that may be used to prepare isoflavonoid-containing protein products is soybean. "Soy protein products" can include, but are not limited to, those items listed in Table 1. "Soy protein products".

TABLE 1

| Soy Protein Products Derived from Soybean Seeds[a] |
|---|
| Whole Soybean Products |
| Roasted Soybeans |
| Baked Soybeans |
| Soy Sprouts |
| Soy Milk |
| Specialty Soy Foods/Ingredients |
| Soy Milk |
| Tofu |
| Tempeh |
| Miso |
| Soy Sauce |
| Hydrolyzed Vegetable Protein |
| Whipping Protein |
| Processed Soy Protein Products |
| Full Fat and Defatted Flours |
| Soy Grits |
| Soy Hypocotyls |
| Soybean Meal |
| Soy Milk |
| Soy Protein Isolates |
| Soy Protein Concentrates |
| Textured Soy Proteins |
| Textured Flours and Concentrates |
| Textured Concentrates |
| Textured Isolates |

[a]See Soy Protein Products: Characteristics, Nutritional Aspects and Utilization (1987). Soy Protein Council.

"Processing" refers to any physical and chemical methods used to obtain the products listed in Table 1 and includes, but is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991-1992). Products referred to as being "high protein" or "low protein" are those as described by these Standard Specifications. "NSI" refers to the Nitrogen Solubility Index as defined by the American Oil Chemists' Society Method Ac4 41. "KOH Nitrogen Solubility" is an indicator of soybean meal quality and refers to the amount of nitrogen soluble in 0.036 M KOH under the conditions as described by Araba and Dale [(1990) *Poult. Sci.* 69:76-83]. "White" flakes refer to flaked, dehulled cotyledons that have been defatted and treated with controlled moist heat to have an NSI of about 85 to 90. This term can also refer to a flour with a similar NSI that has been ground to pass through a No. 100 U.S. Standard Screen size. "Cooked" refers to a soy protein product, typically a flour, with an NSI of about 20 to 60. "Toasted" refers to a soy protein product, typically a flour, with an NSI below 20. "Grits" refer to defatted, dehulled cotyledons having a U.S. Standard screen size of between No. 10 and 80. "Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass [(1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302-338]. "Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously [Atkinson (1970) U.S. Pat. No. 3,488,770, Horan (1985) In *New Protein Foods*, ed. by Altschul and Wilcke, Academic Press, Vol. 1A, Chapter 8, pp 367-414]. Moreover, conditions used during extrusion processing of complex foodstuff mixtures that include soy protein products have been described previously [Rokey (1983) *Feed Manufacturing Technology III*, 222-237; McCulloch, U.S. Pat. No. 4,454, 804].

Also, within the scope of this invention are food, food supplements, food bars, and beverages that have incorporated therein an isoflavonoid-containing product of the invention. The beverage can be in a liquid or in a dry powdered form.

The isoflavonoid-containing product made according to the process of the present invention can be incorporated into a wide variety of food and beverage applications. For example, it can be integrated into meats such as ground meats, emulsified meats, marinated meats, and meats injected with the soy product of the invention; it can also be incorporated into nutritional supplements; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; and salad dressings; and dips and spreads such as mayonnaise; and chip dips; and food bars.

The isoflavonoid-containing product of the invention may also be incorporated into a cereal food product, a snack food product, a baked good product, a fried food product, a health food product, an infant formula, a beverage, a nutritional supplement, a dairy product, a pet food product, or animal feed.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to, whole grain, crushed grain, grits, flour, bran, germ, breakfast cereals, extruded foods, pastas, and the like.

A baked good product comprises any of the cereal food products mentioned above and has been baked or processed in a manner comparable to baking, i.e., to dry or harden by subjecting to heat. Examples of a baked good product include, but are not limited to bread crumbs, baked snacks, mini-biscuits, mini-crackers, mini-cookies, and mini-pretzels.

A snack food product comprises any of the above or below described food products.

A fried food product comprises any of the above or below described food products that has been fried.

A health food product is any food product that imparts a health benefit. Many oilseed-derived food products may be considered as health foods.

The beverage can be in a liquid or in a dry powdered form.

For example, there can be mentioned non-carbonated drinks; carbonated drinks; fruit juices, fresh, frozen, canned or concentrate; still or sparkling water; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. They serve as substitutes for human milk. Infant formulas have a special role to play in the diets of infants because they are often the only source of nutrients for infants. Although breast-feeding is still the best nourishment for infants, infant formula is a close enough second that babies not only survive but thrive. Infant formula is becoming more and more increasingly close to breast milk.

A dairy product is a product derived from milk. These products include, but are not limited to, whole milk, skim milk, fermented milk products such as yogurt or sour milk, cream, butter, condensed milk, dehydrated milk, coffee whitener, ice cream, cheese, whey products, lactose, etc.

In still another aspect this invention concerns a method of producing an isoflavonoid-containing product which comprises: (a) cracking the seeds obtained from transformed plants of the invention to remove the meats from the hulls; and (b) flaking the meats obtained in step (a) to obtain the desired flake thickness.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Construction of Plasmids for Transformation of *Glycine Max*

The ability to alter the ratio of individual isoflavonoids in transgenic plants was tested. For this purpose, a vector (plasmid AC23) was prepared that would be capable of suppressing chalcone reductase.

Preparation of Plasmid AC23

Figure 2:
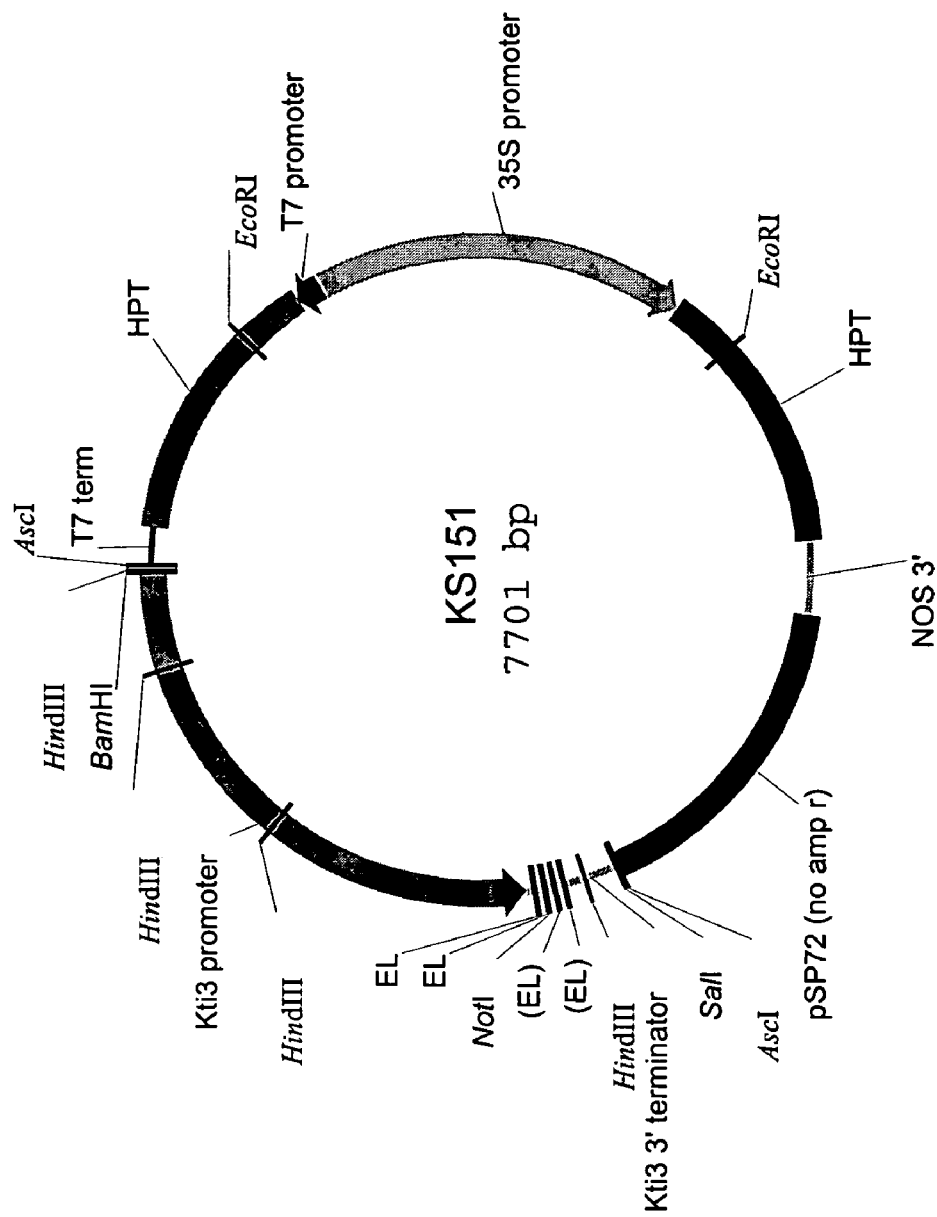
FIG. 2 depicts a representation of the seed-specific expression vector pKS151. The two copies of the 36-nucleotide sequence are indicated by "EL", and the inverted-repeat of the 36-nucleotide sequences is indicated by "(EL)".

Plasmid AC23 contains a seed-specific expression promoter followed by nucleotides that promote formation of a stem loop structure flanking nucleotides encoding a portion of a soybean chalcone reductase, and followed by a transcription termination signal. It is well understood by those skilled in the art that other sequences commonly used in molecular manipulations may be used here. These sequences may include any seed-specific promoter, any structure that promotes stem-loop formation, any polynucleotide encoding any portion of the gene or genes of interest inserted in sense or anti-sense orientation with respect to the promoter and stem-loop structure, and any termination signal. It is also well known by those skilled in the art that nucleotides promoting stem-loop formation are not always required for gene suppression. Plasmid AC23 was prepared as follows:

A polynucleotide encoding a portion of a soybean chalcone reductase was inserted in the seed-specific expression vector pKS151 to obtain plasmid AC23. Vector pKS151 is depicted in FIG. 2 and its nucleotide sequence is shown in SEQ ID NO:1. This vector has been described in PCT Publication WO 02/00904, published 3 Jan. 2002, and is derived from the commercially available vector pSP72 (Promega, Madison, Wis.).

Vector pSP72 was modified as follows to produce plasmid pKS151:

a) deleting the polynucleotide fragment corresponding to the beta lactamase coding region (nucleotides 1135 through 1995 corresponding);

b) inserting a polynucleotide fragment encoding HPT under the control of the T7 promoter and termination signals, for expression of the HPT enzyme in bacteria;

c) adding a polynucleotide consisting essentially of the CaMV 35S promoter/HPT/NOS 3' for constitutive expression of the HPT enzyme in plants; and d) adding a polynucleotide consisting essentially of a unique Not 1 restriction endonuclease site surrounded by nucleotides that promote formation of a stem structure which are flanked by the KTi promoter and KTi 3' terminator.

Expression of HPT by two different promoters allows the selection for growth in the presence of hygromycin in bacterial and plant systems. The gene encoding the kunitz trypsin inhibitor 3 (KTi3) has been described (Jofuku and Goldberg (1989) *Plant Cell* 1:1079-1093). In plasmid pKS151 the KTi3 promoter includes about 2088 nucleotides upstream (5') from the translation initiation codon, and the KTi3 terminator includes about 202 nucleotides downstream (3') from the translation stop codon of KTi 3. Between the KTi3 5' and 3' regions is a unique Not I restriction endonuclease site. The Not I site is flanked by nucleotides that promote formation of a "stem-loop" structure when a polynucleotide from the gene of interest is inserted at the Not I site. The nucleotides promoting the formation of a stem are shown in SEQ ID NO:7. This "stem-loop" structure will have the polynucleotides from the gene of interest forming the loop. The stem structure is formed by two copies of 36 nucleotides at the 5' end of the Not I site and an inverted repeat of the same two 36-nucleotide copies at the 3' end.

Sequences encoding a portion of a soybean chalcone reductase were inserted in the Not I site of pKS151 to create plasmid AC23. The fragment corresponding to a portion of the chalcone reductase coding sequence was obtained by PCR amplification using clone src3c.pk009.e4 as template and primers chalcone reductase-Not1-sense (shown in SEQ ID NO:2) and chalcone reductase-Not1-antisense (shown in SEQ ID NO:3). The nucleotide sequence of the cDNA insert in clone src3c.pk009.e4 is shown in SEQ ID NO:4.

(SEQ ID NO:2)
5'-GCG GCC GCA TGG CTG CTG CTA TTG AAA TC-3'

(SEQ ID NO:3)
5"-GCG GCC GCC CTG CTC GCA CCT TTC CTC AG-3'

The amplification reaction was performed using advantage 2 polymerase and GC melt reagent (1 mM final concentration) and following the manufacturer's (Clontech, Palo Alto, Calif.) protocol. The resulting amplified DNA fragment was first cloned into TopoTA vector (Invitrogen, Carlsbad, Calif.). The fragment was liberated from the TopoTA vector by Not I digestion and was purified from an agarose gel using Qiagen Gel Purification Kit (Qiagen, Valencia, Calif.). The purified DNA fragment was inserted into the Not I site of vector pKS151 to produce the plasmid AC23.

Example 2

Transformation of Somatic Soybean Embryo Cultures and Regeneration of Soybean Plants The ability to increase the isoflavonoid levels in transgenic soybean plants was tested by transforming soybean somatic embryo cultures with plasmid AC23, selecting transformants that grew in the presence of hygromycin, allowing plants to regenerate, and measuring the levels of isoflavone produced in seeds.

Soybean embryogenic suspension cultures were transformed with plasmid AC23 by the method of particle gun bombardment.

The following stock solutions and media were used for transformation and regeneration of soybean plants:

Stock Solutions (Per Liter):

MS Sulfate 100× stock: 37.0 g $MgSO_4.7H_2O$, 1.69 g $MnSO_4.H_2O$, 0.86 g $ZnSO_4.7H_2O$, 0.0025 g $CuSO_4.5H_2O$.

MS Halides 100× stock: 44.0 g $CaCl_2.2H_2O$, 0.083 g KI, 0.00125 g $COCl_2.6H_2O$, 17.0 g $KH_2PO_4$, 0.62 g $H_3BO_3$, 0.025 g $Na_2MoO_4.2H_2O$, 3,724 g $Na_2EDTA$, 2.784 g $FeSO_4.7H_2O$.

B5 Vitamin stock: 100.0 g myo-inositol, 1.0 g nicotinic acid, 1.0 g pyridoxine HCl, 10.0 g thiamine.

2,4-D stock: 10 mg/mL

Media (per Liter):

SB55: 10 mL of each MS stock, 1 mL of B5 Vitamin stock, 0.8 g $NH_4NO_3$, 3.033 g $KNO_3$, 1 mL 2,4-D stock, 0.667 g asparagine, pH 5.7.

SB103: 1 pk. Murashige & Skoog salt mixture (Gibco, Carlsbad, Calif.), 60 g maltose, 2 g gelrite, pH 5.7.

SB71-1: B5 salts, 1 ml B5 vitamin stock, 30 g sucrose, 750 mg MgCl2, 2 g gelrite, pH 5.7.

Soybean (of the Jack variety) embryogenic suspension cultures were maintained in 35 mL SB55 liquid media on a rotary shaker (150 rpm) at 28° C. with a mix of fluorescent and incandescent lights providing a 16 hour day, 8 hour night cycle. Cultures were subcultured every 2 to 3 weeks by inoculating approximately 35 mg of tissue into 35 mL of fresh liquid media.

Soybean embryonic suspension cultures were transformed by the method of particle gun bombardment (see Klein et al. (1987) *Nature* 327:70-73) using a DuPont Biolistic PDS1000/He instrument. Embryos were bombarded with plasmid pAC23 in a 1:10 molar ratio. Transformed lines were selected on medium containing hygromycin, and the presence of plasmid pAC23 was determined by PCR. Transgenic plants were generated from lines positive for the desired recombinant DNA fragments.

For bombardment, 5 µL of 1 µg/µL plasmid pAC23 DNA, 50 µL 2.5 M $CaCl_2$, and 20 µL 0.1 M spermidine were added to 50 µL of a 60 mg/mL 0.6 µm gold particle suspension. The particle preparation was agitated for 3 minutes, spun in a microfuge for 10 seconds and the supernatant removed. The DNA-coated gold particles were then washed once with 400 µL of 100% ethanol, resuspended in 40 µL of anhydrous ethanol, and sonicated three times for 1 second each. Five µL of the DNA-coated gold particles was then loaded on each macro carrier disk. Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded for each experiment and, following bombardment, the tissue was divided in half, placed back into liquid media, and cultured as described above.

Eleven days after bombardment, the liquid media was exchanged with fresh SB55 media containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus, each new line was treated as an independent transformation event. Soybean suspension cultures can be maintained as suspensions of embryos clustered in an immature developmental stage through subculture or can be regenerated into whole plants by maturation and germination of individual somatic embryos.

Transformed embryogenic clusters were removed from liquid culture and placed on SB103 solid agar media containing no hormones or antibiotics. Embryos were cultured for eight weeks at 26° C. with mixed fluorescent and incandescent lights on a 16 hour day, 8 hour night schedule. During this period, individual embryos were removed from the clusters and analyzed at various stages of embryo development. Lines selected for hygromycin resistance were assayed by PCR for the presence of the CHR construct contained in plasmid pAC23. The presence of the CHR construct was assayed by amplifying plant tissue using Primer 3 (shown in SEQ ID NO:5) and Primer 4 (shown in SEQ ID NO:6)

```
                                        (SEQ ID NO:5)
primer 3: 5'-CAC GGG ACG GAT GGT AGC AAC A-3'

(SEQ ID NO:6)
primer 4: 5'-CCG ATT CTC CCA ACA TTG CTT ATT C-3'
```

Somatic embryos became suitable for germination after eight weeks and were then removed from the maturation medium and dried in empty petri dishes for 1 to 5 days. The dried embryos were then planted in SB71-1 medium where they were allowed to germinate under the same lighting and germination conditions described above. Germinated embryos were transferred to sterile soil and grown to maturity. Seeds were harvested.

Example 3

Analysis of Isoflavone Levels in Seeds of Transformants Containing the CHR Construct The quantity of isoflavones in seeds from transgenic plants comprising the CHR construct was assayed. Seeds were ground, the combined powder was extracted with methanol, hydrolyzed with base, and analyzed. Base hydrolysis converts both malonylglucoside conjugates and acetylglucoside conjugates into glucoside conjugates (genistin, daidzin, and glycitin). Total glucoside conjugates are then measured. While aglycones are not measured by this method the amount of aglycones present is in such low quantities as to not affect the final results. The isoflavone numbers are reported as parts-per-million (ppm) of glucoside conjugates in soybean. A more detailed explanation of the preparation of seed extracts and measurement of isoflavones follows.

Five to eight seeds per transformant were combined and the seeds were ground to a fine powder using a single seed grinder set to the finest setting. One gram of ground soybean seeds was extracted with 40 mL MeOH:water (80:20 v/v) in a 125-mL Erlenmeyer flask at 65° C. on an orbital shaker. After shaking for 2 hours the flask was removed from the shaker and allowed to cool to room temperature. Three mL of 2N NaOH were then added and the flask was returned to an orbital shaker at room temperature for 10 min. The flask was then removed from the shaker and 1-mL glacial acetic acid was added. The sample was diluted to 50 mL with MeOH:water (80:20 v/v) and filtered through 5 pM filter paper in a funnel into another 125-mL Erlenmeyer flask. A mixture of 2.5 mL of sample and 2.5 mL of MeOH:water (80:20 v/v) were diluted with water to 10 mL in a volumetric flask. Particulate material was removed from a sample of 1-1.5 mL by spinning in a microfuge tube, the liquid transferred to a labeled autosampler vial, and analyzed by HPLC using the gradient indicated on Table 2 below.

TABLE 2

| HPLC Gradient Settings | | | |
|---|---|---|---|
| Time (min) | Flow (mL/min) | 1% acetic acid in water (mL) | 1% acetic acid in acetonitrile (mL) |
| Initial | 1.0 | 90 | 10 |
| 5.0 | 1.0 | 90 | 10 |
| 11.0 | 1.0 | 78 | 22 |
| 12.0 | 2.0 | 0 | 100 |
| 14.5 | 2.0 | 0 | 100 |
| 14.6 | 2.0 | 90 | 10 |
| 16.5 | 1.0 | 90 | 10 |

The HPLC was set to continue acquiring data to 17 minutes. Degas mode was set to continuous, column temperature was set to 30° C., and sample temperature was set to 4° C. The ultraviolet detector was set as follows: sampling rate=10, wavelength=262 nm, autozero=0.1 minutes. The amounts of isoflavones present were determined by comparing the results to a 5-point standard curve conducted using commercially available daidzin, glycitin, and genistin.

Analysis of R1 Seed from Transformation Events with Plasmid AC23

The levels of isoflavones in R1 seed from 88 plants derived from 46 independent transformation events were assayed. These plants all contained plasmid AC23. Each assay was performed using 5 to 8 seeds from each transformed plant as described above. Table 3 presents the level of isoflavone components (daidzin, glycitin, or genistin), the sum of all isoflavones (total), as well as the sum of daidzin and glycitin (D+Gy), of samples of transgenic seeds positive for the CHR construct. Isoflavone levels are reported as parts-per-million (ppm).

TABLE 3

Isoflavone and Isoflavone Component Levels in R1 Seed Transgenic for Plasmid AC23

| Plant No. | Daidzin (ppm) | Glycitin (ppm) | Genistin (ppm) | D + Gy (ppm) | Total (ppm) |
|---|---|---|---|---|---|
| 3058-2-1-1 | 587 | 370 | 845 | 957 | 1802 |
| 3058-2-1-2 | 817 | 511 | 1241 | 1328 | 2569 |
| 3058-2-2-1 | 652 | 467 | 971 | 1119 | 2090 |
| 3058-2-2-2 | 444 | 358 | 922 | 802 | 1725 |
| 3058-2-3-1 | 763 | 458 | 1277 | 1221 | 2498 |
| 3058-2-4-1 | 824 | 724 | 1372 | 1548 | 2921 |
| 3058-2-4-2 | 602 | 532 | 1278 | 1134 | 2412 |
| 3058-2-4-3 | 979 | 714 | 1969 | 1693 | 3661 |
| 3058-2-5-1 | 468 | 516 | 1186 | 984 | 2170 |
| 3058-2-5-2 | 552 | 623 | 1631 | 1175 | 2806 |
| 3058-3-1-1 | 1139 | 731 | 1763 | 1870 | 3632 |
| 3058-3-1-2 | 1000 | 753 | 1537 | 1753 | 3289 |
| 3058-3-2-1 | 936 | 1040 | 1508 | 1976 | 3483 |
| 3058-3-2-2 | 1099 | 1074 | 1667 | 2173 | 3841 |
| 3058-3-3-1 | 1640 | 869 | 2903 | 2509 | 5413 |
| 3058-3-3-2 | 1132 | 726 | 1753 | 1858 | 3611 |
| 3058-3-4-1 | 815 | 592 | 1193 | 1407 | 2600 |
| 3058-3-4-2 | 1092 | 631 | 1571 | 1723 | 3294 |
| 3058-3-6-2 | 1126 | 1063 | 2069 | 2189 | 4258 |
| 3058-3-6-3 | 785 | 888 | 2465 | 1673 | 4137 |
| 3058-3-8-1 | 298 | 250 | 1828 | 548 | 2376 |
| 3058-3-8-2 | 726 | 497 | 2405 | 1223 | 3627 |
| 3058-4-1-1 | 505 | 649 | 1342 | 1154 | 2495 |
| 3058-4-1-2 | 582 | 638 | 1494 | 1220 | 2713 |
| 3058-4-2-1 | 632 | 495 | 1408 | 1127 | 2534 |
| 3058-4-2-2 | 558 | 479 | 1317 | 1037 | 2353 |
| 3058-4-2-3 | 495 | 503 | 1305 | 998 | 2303 |
| 3058-5-2-1 | 859 | 790 | 1454 | 1649 | 3103 |
| 3058-5-2-2 | 1064 | 697 | 1686 | 1761 | 3447 |
| 3058-6-3-1 | 391 | 358 | 827 | 749 | 1577 |
| 3058-6-3-2 | 390 | 390 | 744 | 780 | 1523 |
| 3058-6-2-1 | 848 | 767 | 1870 | 1615 | 3485 |
| 3058-6-2-2 | 546 | 405 | 1796 | 951 | 2748 |
| 3063-1-1-1 | 885 | 1103 | 1458 | 1988 | 3445 |
| 3063-1-1-2 | 1003 | 940 | 1628 | 1943 | 3572 |
| 3063-1-2-1 | 1344 | 873 | 2045 | 2217 | 4262 |
| 3063-1-2-2 | 1156 | 487 | 1902 | 1643 | 3544 |
| 3063-1-4-1 | 523 | 643 | 884 | 1166 | 2050 |
| 3063-1-5-1 | 401 | 275 | 2619 | 676 | 3295 |
| 3063-1-5-2 | 458 | 518 | 1643 | 976 | 2619 |
| 3063-1-6-1 | 849 | 602 | 1660 | 1451 | 3111 |
| 3063-1-6-3 | 1333 | 750 | 2565 | 2083 | 4648 |
| 3063-1-7-2 | 168 | 235 | 1823 | 403 | 2226 |
| 3063-1-7-3 | 116 | 174 | 1270 | 290 | 1560 |
| 3063-2-10-1 | 202 | 338 | 1276 | 540 | 1815 |
| 3063-2-10-2 | 218 | 339 | 1590 | 557 | 2147 |
| 3063-2-1-1 | 468 | 390 | 936 | 858 | 1794 |
| 3063-2-11-2 | 791 | 513 | 1457 | 1304 | 2761 |
| 3063-2-12-1 | 299 | 293 | 1679 | 592 | 2271 |
| 3063-2-12-2 | 342 | 366 | 1647 | 708 | 2355 |
| 3063-2-12-3 | 364 | 343 | 2243 | 707 | 2950 |
| 3063-2-4-2 | 555 | 467 | 1166 | 1022 | 2188 |
| 3063-2-5-1 | 843 | 697 | 1920 | 1540 | 3459 |
| 3063-2-5-2 | 677 | 745 | 1653 | 1422 | 3074 |

TABLE 3-continued

Isoflavone and Isoflavone Component Levels in R1 Seed Transgenic for Plasmid AC23

| Plant No. | Daidzin (ppm) | Glycitin (ppm) | Genistin (ppm) | D + Gy (ppm) | Total (ppm) |
|---|---|---|---|---|---|
| 3063-2-6-3 | 476 | 202 | 1258 | 678 | 1937 |
| 3063-2-8-1 | 1481 | 667 | 3005 | 2148 | 5153 |
| 3063-2-8-2 | 1070 | 671 | 2193 | 1741 | 3933 |
| 3063-2-9-1 | 425 | 495 | 1835 | 920 | 2755 |
| 3063-2-9-2 | 406 | 543 | 2080 | 949 | 3030 |
| 3063-3-1-1 | 474 | 699 | 1045 | 1173 | 2219 |
| 3063-3-1-2 | 654 | 565 | 1386 | 1219 | 2605 |
| 3063-3-2-1 | 525 | 595 | 923 | 1120 | 2043 |
| 3063-3-2-2 | 423 | 397 | 901 | 820 | 1722 |
| 3063-3-3-1 | 543 | 648 | 1029 | 1191 | 2220 |
| 3063-3-3-2 | 590 | 667 | 1204 | 1257 | 2461 |
| 3063-3-4-1 | 627 | 665 | 1732 | 1292 | 3024 |
| 3063-3-4-2 | 450 | 451 | 1268 | 901 | 2169 |
| 3063-3-5-1 | 530 | 347 | 1062 | 877 | 1938 |
| 3063-3-5-2 | 499 | 506 | 1232 | 1005 | 2237 |
| 3063-3-7-1 | 692 | 789 | 1623 | 1481 | 3104 |
| 3063-3-7-2 | 939 | 710 | 2102 | 1649 | 3751 |
| 3063-4-1-1 | 761 | 569 | 1256 | 1330 | 2585 |
| 3063-4-1-2 | 773 | 581 | 1402 | 1354 | 2756 |
| 3063-4-3-1 | 876 | 914 | 1390 | 1790 | 3181 |
| 3063-4-3-2 | 611 | 515 | 1102 | 1126 | 2228 |
| 3063-4-4-1 | 206 | 352 | 1668 | 558 | 2225 |
| 3063-4-4-3 | 187 | 493 | 622 | 680 | 1302 |
| 3063-4-5-1 | 588 | 744 | 884 | 1332 | 2216 |
| 3063-4-5-2 | 639 | 595 | 1174 | 1234 | 2408 |
| 3063-4-6-1 | 877 | 788 | 1686 | 1665 | 3352 |
| 3063-4-6-2 | 616 | 743 | 1180 | 1359 | 2540 |
| 3063-6-3-1 | 672 | 548 | 1301 | 1220 | 2521 |
| 3063-6-3-2 | 555 | 638 | 1022 | 1193 | 2215 |
| 3063-6-5-1 | 278 | 348 | 578 | 626 | 1204 |
| 3063-6-5-2 | 534 | 648 | 861 | 1182 | 2043 |
| 3063-6-7-1 | 498 | 357 | 2491 | 855 | 3346 |
| 3063-6-7-2 | 778 | 634 | 3065 | 1412 | 4477 |
| 3063-6-8-1 | 284 | 348 | 561 | 632 | 1193 |

Figure 3:
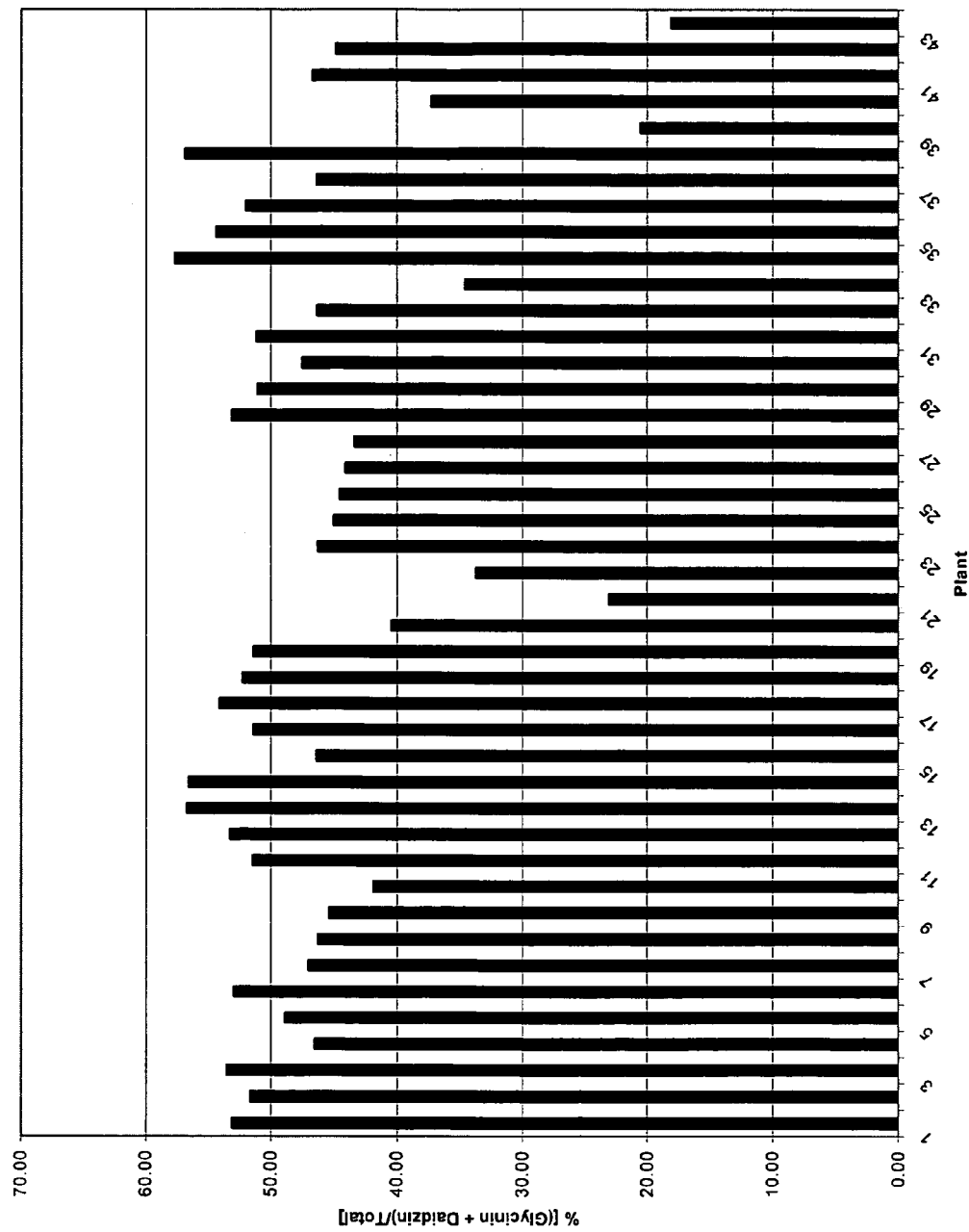
FIGS. 3 and 4 depict the percentage of total isoflavones that the sum of daidzin and glycitin represent in bulk R1 seeds from transformed plants containing the CHR construct. This percentage was determined using the equation: 100((daidzin+glycitin)/total isoflavones).
Figure 4:
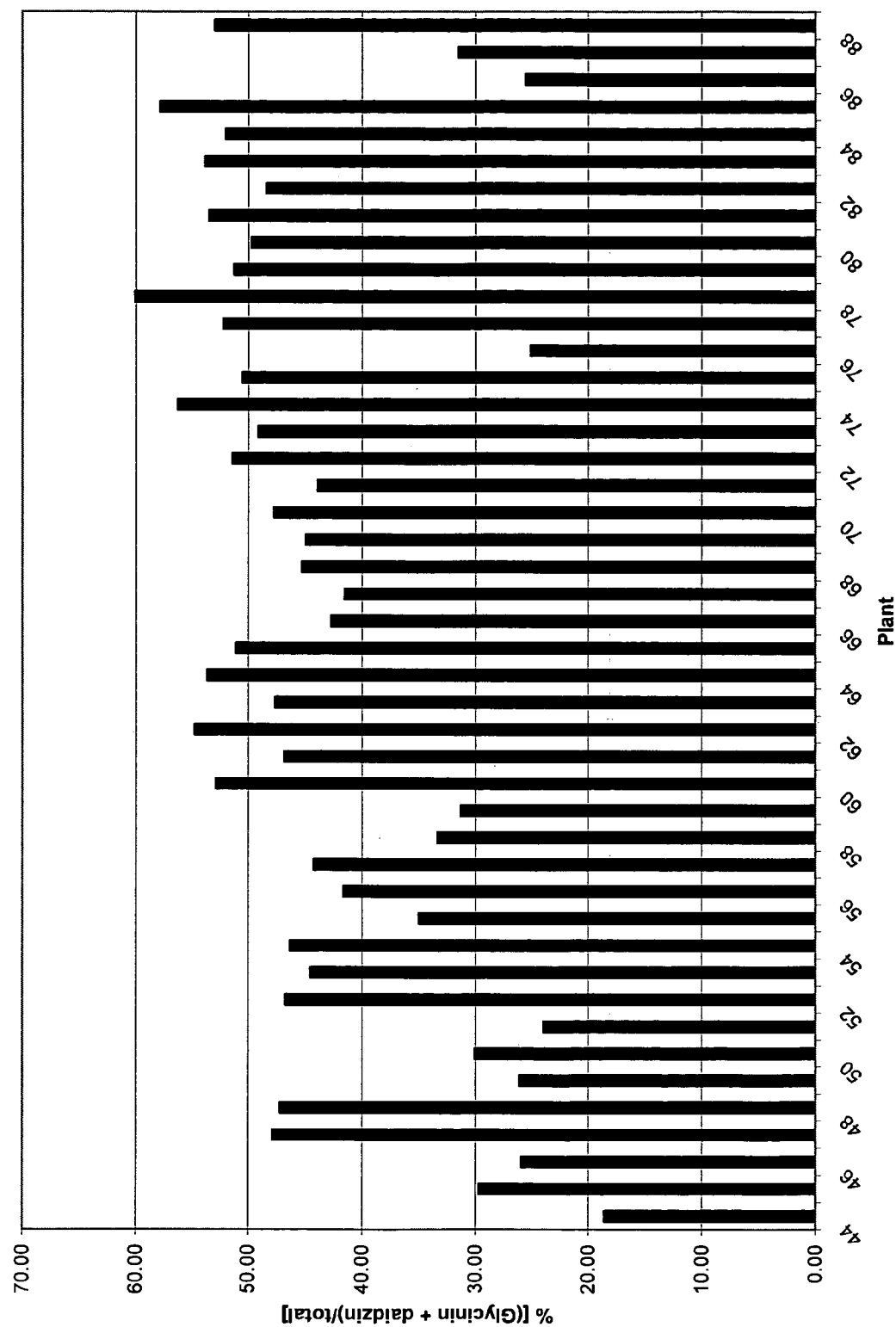

The ratio of the sum of daidzin and glycitin to total isoflavones (D+Gy/T) was calculated for the same plants listed in Table 3 and are listed in Table 4. FIG. 3 presents the results obtained for plants 1-44 and FIG. 4 presents the results obtained for plants 45-88. For ease of understanding, the plants from which the seeds are derived are numbered 1 through 88 in the figures, and the plant number indicated in the table.

TABLE 4

Ratio of the Sum of Daidzin and Glycitin to Total Isoflavones in R1 Seed Transgenic for Plasmid AC23

| Plant | Plant No. | (D + Gy/T)100 |
|---|---|---|
| 1 | 3058-2-1-1 | 53.11 |
| 2 | 3058-2-1-2 | 51.69 |
| 3 | 3058-2-2-1 | 53.54 |
| 4 | 3058-2-2-2 | 46.49 |
| 5 | 3058-2-3-1 | 48.88 |
| 6 | 3058-2-4-1 | 53.00 |
| 7 | 3058-2-4-2 | 47.01 |
| 8 | 3058-2-4-3 | 46.24 |
| 9 | 3058-2-5-1 | 45.35 |
| 10 | 3058-2-5-2 | 41.87 |
| 11 | 3058-3-1-1 | 51.49 |
| 12 | 3058-3-1-2 | 53.30 |
| 13 | 3058-3-2-1 | 56.73 |
| 14 | 3058-3-2-2 | 56.57 |
| 15 | 3058-3-3-1 | 46.35 |
| 16 | 3058-3-3-2 | 51.45 |
| 17 | 3058-3-4-1 | 54.12 |
| 18 | 3058-3-4-2 | 52.31 |

TABLE 4-continued

Ratio of the Sum of Daidzin and Glycitin to Total Isoflavones in R1 Seed Transgenic for Plasmid AC23

| Plant | Plant No. | (D + Gy/T)100 |
|---|---|---|
| 19 | 3058-3-6-2 | 51.41 |
| 20 | 3058-3-6-3 | 40.44 |
| 21 | 3058-3-8-1 | 23.06 |
| 22 | 3058-3-8-2 | 33.72 |
| 23 | 3058-4-1-1 | 46.25 |
| 24 | 3058-4-1-2 | 44.97 |
| 25 | 3058-4-2-1 | 44.48 |
| 26 | 3058-4-2-2 | 44.07 |
| 27 | 3058-4-2-3 | 43.33 |
| 28 | 3058-5-2-1 | 53.14 |
| 29 | 3058-5-2-2 | 51.09 |
| 30 | 3058-6-3-1 | 47.50 |
| 31 | 3058-6-3-2 | 51.21 |
| 32 | 3058-6-2-1 | 46.34 |
| 33 | 3058-6-2-2 | 34.61 |
| 34 | 3063-1-1-1 | 57.71 |
| 35 | 3063-1-1-2 | 54.40 |
| 36 | 3063-1-2-1 | 52.02 |
| 37 | 3063-1-2-2 | 46.36 |
| 38 | 3063-1-4-1 | 56.88 |
| 39 | 3063-1-5-1 | 20.52 |
| 40 | 3063-1-5-2 | 37.27 |
| 41 | 3063-1-6-1 | 46.64 |
| 42 | 3063-1-6-3 | 44.81 |
| 43 | 3063-1-7-2 | 18.10 |
| 44 | 3063-1-7-3 | 18.59 |
| 45 | 3063-2-10-1 | 29.75 |
| 46 | 3063-2-10-2 | 25.94 |
| 47 | 3063-2-1-1 | 47.83 |
| 48 | 3063-2-11-2 | 47.23 |
| 49 | 3063-2-12-1 | 26.07 |
| 50 | 3063-2-12-2 | 30.06 |
| 51 | 3063-2-12-3 | 23.97 |
| 52 | 3063-2-4-2 | 46.71 |
| 53 | 3063-2-5-1 | 44.52 |
| 54 | 3063-2-5-2 | 46.26 |
| 55 | 3063-2-6-3 | 35.00 |
| 56 | 3063-2-8-1 | 41.68 |
| 57 | 3063-2-8-2 | 44.27 |
| 58 | 3063-2-9-1 | 33.39 |
| 59 | 3063-2-9-2 | 31.32 |
| 60 | 3063-3-1-1 | 52.86 |
| 61 | 3063-3-1-2 | 46.79 |
| 62 | 3063-3-2-1 | 54.82 |
| 63 | 3063-3-2-2 | 47.62 |
| 64 | 3063-3-3-1 | 53.65 |
| 65 | 3063-3-3-2 | 51.08 |
| 66 | 3063-3-4-1 | 42.72 |
| 67 | 3063-3-4-2 | 41.54 |
| 68 | 3063-3-5-1 | 45.25 |
| 69 | 3063-3-5-2 | 44.93 |
| 70 | 3063-3-7-1 | 47.71 |
| 71 | 3063-3-7-2 | 43.96 |
| 72 | 3063-4-1-1 | 51.45 |
| 73 | 3063-4-1-2 | 49.13 |
| 74 | 3063-4-3-1 | 56.27 |
| 75 | 3063-4-3-2 | 50.54 |
| 76 | 3063-4-4-1 | 25.08 |
| 77 | 3063-4-4-3 | 52.23 |
| 78 | 3063-4-5-1 | 60.11 |
| 79 | 3063-4-5-2 | 51.25 |
| 80 | 3063-4-6-1 | 49.67 |
| 81 | 3063-4-6-2 | 53.50 |
| 82 | 3063-6-3-1 | 48.39 |
| 83 | 3063-6-3-2 | 53.86 |
| 84 | 3063-6-5-1 | 51.99 |
| 85 | 3063-6-5-2 | 57.86 |
| 86 | 3063-6-7-1 | 25.55 |
| 87 | 3063-6-7-2 | 31.54 |
| 88 | 3063-6-8-1 | 52.98 |

As seen in the table above, the sum of daidzin and glycitin was between 10% and 20% of the total isoflavones in two plants derived from one transformation event positive for plasmid AC23. The sum of daidzin and glycitin was between 20% and 30% of the total isoflavones in eight plants derived from six independent transformation events positive for plasmid AC23. The sum of daidzin and glycitin was between 30% and 40% of the total isoflavones in eight plants from seven independent transformation events positive for plasmid AC23.

The results shown in Table 4 and FIGS. 3 and 4 may be compared with those shown in Table 1 of Wang, C. et al. [(2000) *J. Am. Oil Chem. Soc.* 77:483-487]. The Wang et al. report shows analysis of the agronomic characteristics of 210 soybean cultivars grown in the State of South Dakota in the United States and concludes that the isoflavone contents in non-transgenic soybean plants varies greatly. Table 1 of the Wang report shows the total isoflavones (in µg/g), and the total percent of genistein, daidzein, and glycitein for all 210 soybean cultivars. Addition of the total daidzein percent with the total glycitein percent for each cultivar shows that it varies from a low of 35 (for Golden Harvest H-1263 and Newton 1006) to a high of 54 (for Praire Brand 227EXP). As shown in Table 4 and FIGS. 3 and 4 of the present application, suppression of chalcone reductase results in transgenic plants having even lower levels of daidzin and glycitin than is reported by Wang et al. The isoflavone analyses in the present application were performed using samples containing from 5 to 8 R1 seeds. It is expected that a bulk sample of R1 seeds will contain a combination of wild-type and transgenic seed with, on average, ¼ of the seeds being wild-type. Thus, the levels of daidzin plus glycitin in the transgenic seeds alone will be even lower than what is shown in Table 4 and FIGS. 3 and 4.

The data above shows that suppression of CHR in isoflavonoid-producing plants results in such plants having reduced levels of liquiritigenin-derived isoflavones.

What is claimed is:

1. A method for decreasing the ratio of liquiritigenin-derived isoflavones relative to total isoflavone levels in an isoflavonoid-producing plant the method comprising:
   a) transforming a plant cell with a recombinant construct comprising a promoter operably linked to a nucleic acid sequence of at least 200 nucleotides having at least 95% sequence identity to SEQ ID NO:4;
   b) regenerating a transformed plant from the transformed plant cell of (a); and
   c) evaluating the transformed plant obtained from step (b) for a reduced ratio of liquiritigenin-derived isoflavones relative to total isoflavone levels as compared to the ratio of liquiritigenin-derived isoflavones relative to total isoflavone levels in an untransformed plant.

2. The method of claim 1 wherein the promoter is operably linked, in a sense orientation, to the nucleic acid sequence.

3. The method of claim 1 wherein the promoter is operably linked, in an anti-sense orientation, to the nucleic acid sequence.

4. The method of claim 1 wherein the recombinant construct comprises a stem-loop structure.

5. The method of claim 4 wherein the nucleic acid sequence forms a stem in the stem-loop structure.

6. The method of claim 4 wherein the nucleic acid sequence forms a loop in the stem-loop structure.

7. The method of claim 4 wherein the nucleic acid sequence forms a loop in the stem-loop structure and the stem consists essentially of SEQ ID NO:7.

8. The method of claim 1 wherein the promoter is a seed-specific promoter.

9. The method of claim 1 wherein the isoflavonoid-producing plant is selected from the group consisting of soybean, clover, mung bean, lentil, hairy vetch, alfalfa, lupine, sugar beet, and snow pea.

10. An isoflavonoid-producing plant made by the method of any one of claims 1 to 8 wherein the plant has a reduced ratio of liquiritigenin-derived isoflavones relative to total isoflavone levels as compared to the ratio of liquiritigenin-derived isoflavones relative to total isoflavone levels in an untransformed plant.

11. The isoflavonoid-producing plant of claim 9 wherein the plant is selected from the group consisting of soybean, clover, mung bean, lentil, hairy vetch, alfalfa, lupine, sugar; beet and snow pea.

12. Seeds or plant parts of the plant of claim 11.

13. An isoflavonoid-producing plant comprising in its genome a recombinant construct comprising a promoter operably linked to a nucleic acid sequence of at least 200 nucleotides and having at least 95% sequence identity to SEQ ID NO:4 wherein the plant has a reduced ratio of liquiritigenin-derived isoflavones relative to total isoflavone levels as compared to the ratio of liquiritigenin-derived isoflavones relative to total isoflavone levels in an untransformed plant.

14. The isoflavonoid-producing plant of claim 13 wherein the plant is selected from the group consisting of soybean, clover, mung bean, lentil, hairy vetch, alfalfa, lupine, sugar beet, and snow pea.

15. The plant of claim 14 wherein recombinant construct comprises a promoter operably linked, in sense orientation, to the nucleic acid sequence.

16. The plant of claim 14 wherein recombinant construct comprises a promoter operably linked, in an anti-sense orientation, to the nucleic acid sequence.

17. The plant of claim 14 wherein the recombinant construct comprises a stem-loop structure.

18. The plant of claim 14 wherein the recombinant construct comprises a stem-loop structure in which the nucleic acid sequence forms the stem.

19. The plant of claim 14 the recombinant construct comprises a stem-loop structure in which the nucleic acid sequence forms the loop.

20. The plant of claim 14 wherein the recombinant construct comprises a stem-loop structure in which the nucleic acid sequence forms the loop In the stem-loop structure and the stem consists essentially of SEQ ID NO:7.

21. The plant of claim 14 wherein the recombinant construct comprises a seed-specific promoter.

22. Seeds or plant parts of the plant of any one of claims 14-21 wherein said seeds and said plant parts comprise said construct in their genome.

* * * * *